United States Patent
Rahmani et al.

(10) Patent No.: US 11,635,334 B2
(45) Date of Patent: Apr. 25, 2023

(54) MINIATURE EXTERNAL TEMPERATURE SENSING DEVICE FOR ESTIMATING SUBSURFACE TISSUE TEMPERATURES

(71) Applicant: Apple Inc., Cupertino, CA (US)

(72) Inventors: Helia Rahmani, San Jose, CA (US); Anthony D. Minervini, Sunnyvale, CA (US); Wanfeng Huang, Newark, CA (US); James C. Clements, Campbell, CA (US); Jiandong Yu, Cupertino, CA (US); Zijing Zeng, San Jose, CA (US); Charley T. Ogata, San Jose, CA (US)

(73) Assignee: Apple Inc., Cupertino, CA (US)

( * ) Notice: Subject to any disclaimer, the term of this patent is extended or adjusted under 35 U.S.C. 154(b) by 386 days.

(21) Appl. No.: 16/917,704

(22) Filed: Jun. 30, 2020

(65) Prior Publication Data

US 2021/0404883 A1 Dec. 30, 2021

(51) Int. Cl.
*G01K 3/08* (2006.01)
*G01K 7/00* (2006.01)
(Continued)

(52) U.S. Cl.
CPC ............. *G01K 3/08* (2013.01); *G01K 1/026* (2013.01); *G01K 1/14* (2013.01); *G01K 7/00* (2013.01);
(Continued)

(58) Field of Classification Search
CPC ............ G01K 3/08; G01K 1/026; G01K 1/14; G01K 7/00; G01K 7/427; G01K 13/20; A61B 5/01
See application file for complete search history.

(56) References Cited

U.S. PATENT DOCUMENTS 4,935,345 A * 6/1990 Guilbeau ............... C12Q 1/006
435/14
5,623,594 A * 4/1997 Swamy ..................... G01K 1/14
714/1
(Continued)

FOREIGN PATENT DOCUMENTS

CA 2654084 12/2007
CN 112444322 3/2021
(Continued)

OTHER PUBLICATIONS

Maurer et al., "eWatch: a wearable sensor and notification platform," International Workshop on Wearable and Implantable Body Sensor Networks (BSN'06), Apr. 3-5, 2006, 4 pages.
(Continued)

*Primary Examiner* — Nathaniel T Woodward
*Assistant Examiner* — Philip L Cotey
(74) *Attorney, Agent, or Firm* — Brownstein Hyatt Farber Schreck, LLP

(57) ABSTRACT

Embodiments described herein are directed to a temperature measurement device that includes a sensor body configured to be placed on a skin of a user. The temperature measurement device can include a first section defining a first lower surface and having a first thickness, a second section defining a second lower surface and having a second thickness, and a channel separating the first lower surface from the second lower surface. The temperature measurement device can also include a first set of temperature sensors positioned across the first thickness, a second set of temperature sensors positioned across the second thickness, and a processor configured to estimate a tissue temperature of the user based on comparing temperature signals from the first set of temperature sensors with temperature signals from the second set of temperature sensors.

19 Claims, 7 Drawing Sheets

(51) Int. Cl.
  *G01K 1/14* (2021.01)
  *G01K 1/02* (2021.01)
  *G01K 7/42* (2006.01)
  *G01K 13/20* (2021.01)
  *A61B 5/01* (2006.01)

(52) U.S. Cl.
  CPC ............. *G01K 7/427* (2013.01); *G01K 13/20* (2021.01); *A61B 5/01* (2013.01)

(56) References Cited

U.S. PATENT DOCUMENTS

| | | | | |
|---|---|---|---|---|
| 6,639,395 | B2* | 10/2003 | Male | G01R 19/225 324/105 |
| 6,741,470 | B2* | 5/2004 | Isenburg | H01L 23/4093 257/E23.099 |
| 7,299,090 | B2* | 11/2007 | Koch | G01K 7/42 374/E7.042 |
| 7,416,332 | B2* | 8/2008 | Rountree | G01K 7/00 374/E1.019 |
| 7,622,896 | B2* | 11/2009 | Nakagawa | H02J 7/007192 320/160 |
| 7,852,710 | B2* | 12/2010 | Kelly | G04G 9/0064 368/20 |
| 8,292,495 | B2* | 10/2012 | Bieberich | G01K 1/165 374/208 |
| 8,292,502 | B2* | 10/2012 | Bieberich | G01K 13/20 374/208 |
| 8,304,851 | B2* | 11/2012 | Trifonov | H01L 27/16 257/470 |
| 8,617,381 | B2* | 12/2013 | Sun | G01K 7/16 422/68.1 |
| 8,954,288 | B2* | 2/2015 | Aljabari | G01K 1/20 702/130 |
| 9,304,520 | B2* | 4/2016 | Cheng | G05D 23/1919 |
| 9,438,071 | B1* | 9/2016 | Heiberg | H02J 7/00034 |
| 9,976,914 | B2* | 5/2018 | Radhakrishnan | G01K 7/021 |
| 9,990,172 | B2* | 6/2018 | Komaromi | H04R 25/305 |
| 10,238,301 | B2* | 3/2019 | Weebadde | A61B 5/349 |
| 10,244,985 | B1* | 4/2019 | Sayani | A61B 5/11 |
| 10,309,840 | B2* | 6/2019 | Kalyanasundaram | G01K 13/00 |
| 10,500,087 | B2* | 12/2019 | Thomas | H01L 23/3731 |
| 10,750,951 | B1* | 8/2020 | Prachar | G01K 13/20 |
| 2005/0139250 | A1* | 6/2005 | DeSteese | H01L 35/08 136/212 |
| 2008/0071189 | A1* | 3/2008 | Yarden | G01K 1/165 374/E13.002 |
| 2008/0234004 | A1* | 9/2008 | Loque | H04M 1/72445 455/564 |
| 2011/0119018 | A1* | 5/2011 | Skarp | G01K 7/42 702/130 |
| 2011/0245713 | A1* | 10/2011 | Rensen | G01K 7/02 600/549 |
| 2012/0128024 | A1* | 5/2012 | Tsuchida | G01K 7/42 374/E17.001 |
| 2012/0215113 | A1* | 8/2012 | Yarden | G01K 7/42 600/474 |
| 2013/0107905 | A1* | 5/2013 | Campbell | G06F 1/20 374/1 |
| 2013/0314054 | A1* | 11/2013 | Bergqvist | H02J 7/007194 320/162 |
| 2014/0163765 | A1* | 6/2014 | Jain | G06F 15/00 702/130 |
| 2014/0355649 | A1* | 12/2014 | Niederberger | H04M 1/72454 374/152 |
| 2014/0362889 | A1* | 12/2014 | Jang | G06F 1/206 374/152 |
| 2015/0001965 | A1* | 1/2015 | Angeli | G06F 1/206 324/705 |
| 2015/0241370 | A1* | 8/2015 | Mueller | G06F 3/04186 345/173 |
| 2016/0014554 | A1* | 1/2016 | Sen | H04W 4/02 455/456.2 |
| 2016/0131541 | A1* | 5/2016 | Kim | H04N 5/232411 374/152 |
| 2017/0007167 | A1* | 1/2017 | Kostic | A61B 5/4064 |
| 2017/0074582 | A1* | 3/2017 | Rusnack | G05D 23/1917 |
| 2017/0288452 | A1* | 10/2017 | Adams | H04M 1/0274 |
| 2018/0004169 | A1* | 1/2018 | Matsuzaki | G06F 1/163 |
| 2018/0028072 | A1* | 2/2018 | Shi | A61B 5/6833 |
| 2018/0078170 | A1* | 3/2018 | Panescu | A61B 5/01 |
| 2018/0184908 | A1* | 7/2018 | Meyerson | A61B 5/6833 |
| 2018/0206729 | A1* | 7/2018 | Wang | A61B 5/282 |
| 2018/0242850 | A1* | 8/2018 | Ellis | A61B 5/02007 |
| 2019/0159680 | A1* | 5/2019 | Tanaka | A61B 5/259 |
| 2019/0175024 | A1* | 6/2019 | Lan | A61B 5/0008 |
| 2019/0350531 | A1* | 11/2019 | Shimuta | A61B 5/68335 |
| 2020/0060553 | A1* | 2/2020 | Tsuchimoto | A61B 5/0008 |
| 2020/0229761 | A1* | 7/2020 | Pandya | G04G 21/025 |
| 2021/0121071 | A1* | 4/2021 | Mensch | G16H 50/30 |
| 2021/0186336 | A1* | 6/2021 | Bellifemine | A61B 5/01 |
| 2021/0264346 | A1* | 8/2021 | Momayez | G06Q 50/02 |
| 2021/0278290 | A1* | 9/2021 | Ghoreyshi | A61B 5/746 |
| 2022/0000370 | A1* | 1/2022 | Blom | A61B 5/01 |
| 2022/0087534 | A1* | 3/2022 | Mansky | A61B 5/6892 |

FOREIGN PATENT DOCUMENTS

| | | |
|---|---|---|
| JP | 2012132818 | 7/2012 |
| KR | 20180097191 | 8/2018 |
| WO | WO 13/185679 | 12/2013 |
| WO | WO 18/152566 | 8/2018 |
| WO | WO 20/249665 | 12/2020 |

OTHER PUBLICATIONS

U.S. Appl. No. 17/882,423, filed Aug. 5, 2022, Clements et al.
U.S. Appl. No. 16/935,046, filed Jul. 21, 2020, Clements et al.

* cited by examiner

MINIATURE EXTERNAL TEMPERATURE SENSING DEVICE FOR ESTIMATING SUBSURFACE TISSUE TEMPERATURES

FIELD

The described embodiments relate generally to temperature sensing devices, and more particularly, to an external temperature sensing device configured to estimate subsurface tissue temperatures.

BACKGROUND

Wearable electronic devices, such as smart watch, smart glasses, earphones, and so on, are typically worn by a user throughout the day and may include various sensors to measures physiological parameters of a user and/or environmental parameters. The wearable device can contain various sensing devices for determining one or more physiological parameters of a user such as temperature, heart rate, blood oxygen level, and so on. The sensing devices can include a temperature sensing device, which may be used to measure a temperature of a user. Traditional temperature sensing devices may take a relatively long time (in some cases, minutes) to take a measurement of a user and/or only be able to detect a skin surface temperature of a user. In some cases, it may be desirable to have a wearable or portable electronic device that can more quickly and accurately determine skin or subsurface (e.g., deep tissue) temperature of a user.

SUMMARY

Embodiments herein are directed to a temperature measurement device that includes a sensor body configured to be placed on a skin of a user, where the sensor body includes a first section defining a first lower surface and having a first thickness, and a second section defining a second lower surface and having a second thickness. The sensor body can also define a channel separating the first lower surface from the second lower surface. The temperature measurement device can include a first set of temperature sensors positioned across the first thickness, a second set of temperature sensors positioned across the second thickness, and a processor configured to estimate a tissue temperature of the user based on comparing temperature signals from the first set of temperature sensors with temperature signals from the second set of temperature sensors.

In some cases, the channel is a first channel, and the sensor body further defines a third lower surface positioned between the first and second lower surfaces, and a second channel. The first channel can separate the first lower surface from the third lower surface, and the second channel can separate the second lower surface from the third lower surface. The first set of temperature sensors can have a first temperature sensor positioned on the first lower surface and a second temperature sensor positioned on a first upper surface of the first section. The second set of temperature sensors can have a third temperature sensor positioned on the second lower surface and a fourth temperature sensor positioned on a second upper surface of the second section.

In some examples, the first section defines an upper surface that is opposite the first lower surface. A depth of the channel can extend towards the upper surface. The first section can define a first cylindrical body, and the second section can define a second cylindrical body. In some examples, the second section extends around the first section. The sensor body can be symmetric about an axis, and the channel can extend in a circle around the axis. The sensor body can include a conductive material, and the channel can contain an insulating material. In some cases, a substrate is positioned on the first and second lower surfaces and configured to contact the skin of the user.

Embodiments are also directed to a temperature sensor that includes a sensor body for measuring a temperature of a user. The sensor body can include a first section defining a first lower surface that is offset from a first upper surface, and a second section defining a second lower surface that is offset from a second upper surface. A first thickness between the first lower surface and the first upper surface can be greater than a second thickness between the second lower surface and the second upper surface. A channel can separate the first lower surface from the second lower surface. A first set of temperature sensors can be positioned on the first section, a second set of temperature sensors can be positioned on the second section, and a processor can be configured to estimate a tissue temperature of the user based on comparing temperature signals from the first set of temperature sensors with temperature signals from the second set of temperature sensors.

The first set of temperature sensors can include a first sensor positioned on the first lower surface and a second sensor positioned on the first upper surface. The second set of temperature sensors can include a third sensor positioned on the second lower surface and a fourth sensor positioned on the second upper surface. The first and second lower surfaces can be configured to be placed against a skin of the user. In some cases, the sensor body can further define a third lower surface that is separated from the first lower surface by the first channel, and a second channel that separates the third lower surface from the second lower surface. The sensor body can further define a third channel that separates the first upper surface from the second upper surface. The sensor body can be a conductive material and the first channel can include an insulating material. In some cases, the first section forms a central part of the sensor body and the second section forms an outer part of the sensor body.

Embodiments are also directed to a temperature sensing device that includes a sensor body for measuring a temperature of a user. The sensor body can define first and second lower surfaces that are configured to be placed against a skin of the user. The sensor body can also define a first upper surface offset from and opposite the first lower surface, and a second upper surface offset from and opposite the second lower surface. A first thickness between the first lower surface and the first upper surface can be greater than a second thickness between the second lower surface and the second upper surface, and a channel can be positioned between the first and second lower surfaces. A set of temperature sensors can be configured to measure temperatures at the first lower surface, the second lower surface, the first upper surface, and second upper surface. A processer can be configured to estimate a tissue temperature of the user based on the temperature measurements from the set of temperature sensors.

The channel can be a first channel and the sensor body can further define a third lower surface positioned between the first and second lower surfaces, and a second channel positioned between the first and second lower surfaces. The set of temperature sensors can include a first temperature sensor positioned on the first lower surface, a second temperature sensor positioned on the first upper surface, a third temperature sensor positioned on the second lower surface, and a fourth temperature sensor positioned on the second upper surface. The sensor body can include a conductive material and the channel can include an insulating material.

BRIEF DESCRIPTION OF THE DRAWINGS

The disclosure will be readily understood by the following detailed description in conjunction with the accompanying drawings, wherein like reference numerals designate like structural elements, and in which.

Figure 1:
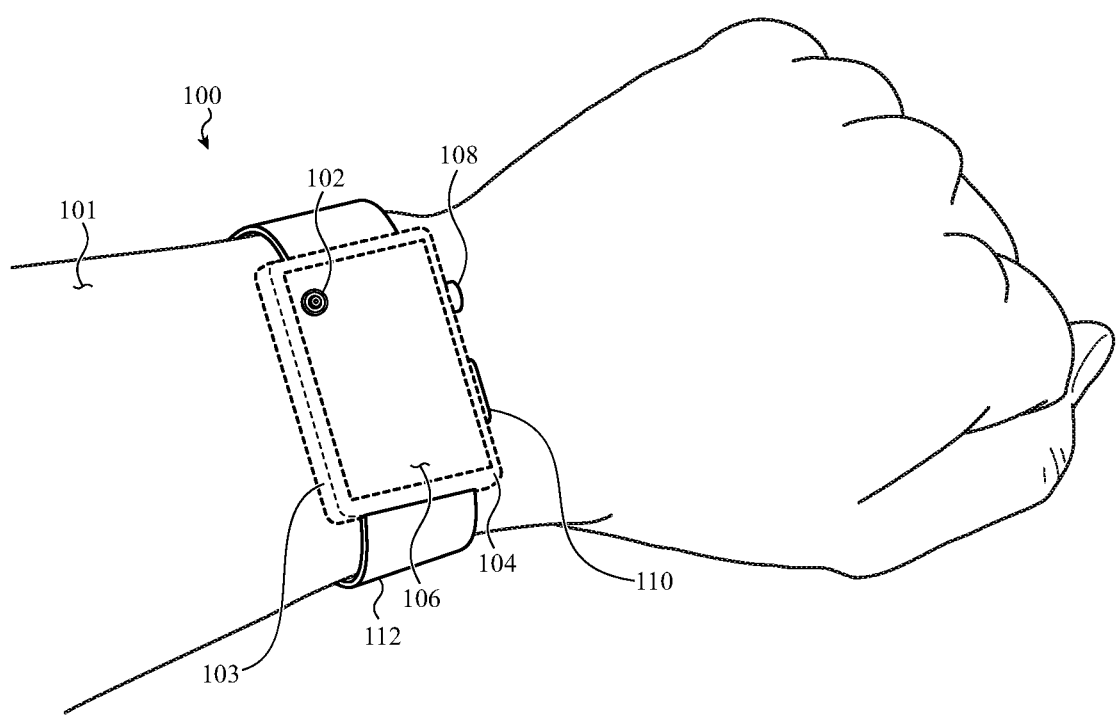
FIG. 1 shows an example electronic device that includes a temperature sensing device.

The use of cross-hatching or shading in the accompanying figures is generally provided to clarify the boundaries between adjacent elements and also to facilitate legibility of the figures. Accordingly, neither the presence nor the absence of cross-hatching or shading conveys or indicates any preference or requirement for particular materials, material properties, element proportions, element dimensions, commonalities of similarly illustrated elements, or any characteristics attribute, or property for any element illustrated in the accompanying figures.

Additionally, it should be understood that the proportions and dimensions (either relative or absolute) of the various features and elements (and collections and groupings thereof) and the boundaries, separations, and positional relationships presented therebetween, are provided in the accompanying figures merely to facilitate an understanding of the various embodiments described herein and, accordingly, may not necessarily be presented or illustrated to scale, and are not intended to indicate any preference or requirement for an illustrated embodiment to the exclusion of embodiments described with reference thereto.

DETAILED DESCRIPTION

Reference will now be made in detail to representative embodiments illustrated in the accompanying drawings. It should be understood that the following descriptions are not intended to limit the embodiments to one preferred embodiment. To the contrary, it is intended to cover alternatives, modifications, and equivalents as can be included within the spirit and scope of the described embodiments as defined by the appended claims.

Embodiments disclosed herein are directed to miniature temperature sensing devices for use in, or incorporation into, portable and/or wearable electronic devices. The temperature sensing device can be used to estimate a subsurface tissue temperature of a user by measuring temperatures at the skin of the user. It may be desirable to estimate subsurface tissue temperatures of a user as these temperatures may be more stable over time and/or accurate in determining a current condition of a user such as whether they have an elevated or depressed temperature.

In some embodiments, the temperature sensing device can have a sensor body that has two sections of different thicknesses and two or more sets of temperature sensors configured to measure temperature differentials across the different sections. Such temperature sensing devices may be referred to as "dual heat flux temperature sensors." Dual heat flux temperature sensors may be placed such that the sensor body is on a surface, such as a skin of a user; the temperature sensor may estimate a subsurface temperature (e.g., a deep tissue temperature of a user) by measuring temperature differences across the two different thicknesses of the sensor body. For example, the sensor body can have an inner cylindrical section that is thicker or taller than an outer toroidal section that extends around a circumference of the inner section, such that the sensor body defines a top hat-like structure. A first set of temperatures sensors can be positioned to measure temperature differences across the thicker, inner cylindrical section and a second set of temperature sensors can be positioned to measure temperature differences across the thinner, outer toroidal section. The temperature differentials across each of these sections can be used to estimate the subsurface tissue temperature of a user. In some cases, additional sets of temperature sensors may be placed at different locations along the first and/or second sections, which may help increase the accuracy of the temperature measurements across each of the sections.

Embodiments described herein are directed to temperature sensing devices that include one or more channels separating a thicker, inner section from a thinner, outer section. The channels can be positioned on a bottom, skin-contacting surface of the sensor body may be ring-shaped to separate a bottom (or skin-contacting) surface of the inner section from a bottom (or skin-contacting) surface of the outer section. The channels can thermally isolate the first section from the second section to reduce heat transfer between the first and second sections. This configuration may provide a greater temperature differential between the first and second sections than if the channels were absent, which, in turn, can improve the accuracy of deep tissue temperature estimations. In some embodiments, the sensor body is formed from a first material such as a metal, polymer, composite material, or the like, and the channel can contain air or another gas that has lower thermal conductivity than the first material. In some cases, the channel can contain a second insulating material such as foam that has lower thermal conductivity than the first material. In certain examples, the channel may be under vacuum.

In some examples, a radial or ring-shaped channel can also be formed on an upper surface of the sensor body and positioned between the thicker, inner section (the "first section") and the thinner, outer section (the "second section"). This upper channel can further reduce heat flow between the first and second sections.

Reducing the heat flow between the first and second sections can allow the temperature sensing device to be decreased in size as compared to similar sensors that lack the insulating channels, while still accurately estimating deep tissue temperature. As previously mentioned, the deep tissue temperature of a user may be estimated by comparing a first temperature differential across the thicker section with a second temperature differential across the second section. As the size of the sensor body is decreased, heat transfer between the thicker section and the thinner section may have a greater impact on each section's temperature differential because the body of the temperature sensor may have smaller thermal gradients across it and thus between sensors, thereby reducing an accuracy of the device. Incorporating channels into the sensor body can reduce heat transfer between these sections to improve the accuracy of dual heat flux temperature sensing devices; this, in turn, permits a dual heat flux temperature sensor to be scaled down while maintaining temperature gradients and thus accuracy. Additionally or alternatively, decreasing the size of the temperature sensing device can decrease the time needed to take the temperature measurements to estimate a deep tissue temperature. These smaller temperature sensing devices can be referred to as "miniature dual heat flux temperature sensors."

Miniature dual heat flux temperature sensors can be incorporated into a variety of electronic devices such as smart watches, mobile phones, tablet computing devices, laptop computing devices, personal digital assistants, digital media players, other wearable devices (including glasses, jewelry, clothing, and earphones), and the like to estimate a deep tissue temperature of a user of the device. For example, a miniature dual heat flux temperature sensor can be incorporated into an electronic device such that it contacts the skin of a user when the electronic device is worn by a user. Temperature measurements from the miniature dual heat flux temperature sensor can be displayed to the user, used by the electronic watch to perform various functions such as a health tracking, and/or combined with other sensor data. In some cases, when incorporated into an electronic device such as a wearable electronic device a miniature dual heat flux temperature sensor can estimate and track deep tissue temperatures of a user over a period of time such as hours, days, months, years, and so on.

These and other embodiments are discussed below with reference to FIGS. 1-7. However, those skilled in the art will readily appreciate that the detailed description given herein with respect to these Figures is for explanatory purposes only and should not be construed as limiting.

FIG. 1 illustrates an electronic device 100 that incorporates a miniature dual heat flux temperature sensing device 102. The electronic device 100 is depicted as an electronic watch (e.g., a smart watch). The body of the watch is shown in phantom to illustrate that the temperature sensing device can be positioned within or partially within an internal chamber of the housing. The watch is one example embodiment of an electronic device and the concepts described herein may apply equally or by analogy to other electronic devices, including mobile phones (e.g., smartphones), tablet computers, notebook computers, head-mounted displays, digital media players (e.g., mp3 players), health-monitoring devices, other portable electronic devices, or the like. The electronic device 100 can incorporate the miniature dual heat flux temperature sensing device 102 as described herein.

The electronic device 100 may be worn by a user 101 and include one more sensors that determine a condition(s) of the user such as a body temperature, heart rate, position, direction of movement, and so on, and/or a condition of the environment such as a barometric pressure, air temperature, moisture level, and so on. Different sensors may be positioned at different locations on or within the electronic device 100 depending on operating requirements of a particular sensor, the condition being detected by the sensor, the design of the electronic device 100, and so on.

The electronic device 100 can include the dual heat flux temperature sensors 102 that are configured to estimate a deep tissue temperature of the user 101 by measuring temperatures of the skin of the user 101. The electronic device 100 can include a housing 103 and cover 104 coupled to the housing 103. The cover 104 can be transparent and positioned over a display 106. The housing 103, the cover 104, along with other components, may form a sealed internal chamber or volume of the electronic device 100. The cover 104 can also define an input surface of the electronic device 100. For example, as described herein, the electronic device 100 may include touch and/or force sensors that detect inputs applied to the cover 104. The cover 104 may be formed from or include glass, sapphire, polymer, dielectric, or any other suitable material.

The display 106 can be positioned under the cover 104 and at least partially within the housing 103. The display 106 can define an output region in which graphical outputs are displayed. Graphical outputs may include graphical user interfaces, user interface elements (e.g., buttons, sliders, etc.), text, lists, photographs, animations, videos, or the like. The display 106 can include a liquid-crystal display (LCD), organic light emitting diode (OLED) display, or any other suitable components or display technology. In some cases, the display 106 can output a graphical user interface with one or more graphical objects that display information collected from or derived from the pressure-sensing system. For example, the display 106 can output a current barometric pressure associated with the electronic device 100 or estimated altitude of the electronic device 100.

The display 106 may include or be associated with touch sensors and/or force sensors that extend along the output region of the display and which may use any suitable sensing elements and/or sensing techniques. Using touch sensors, the electronic device 100 may detect touch inputs applied to the cover 104, including detecting locations of touch inputs, motions of touch inputs (e.g., the speed, direction, or other parameters of a gesture applied to the cover 104), or the like. Using force sensors, the device 100 may detect amounts or magnitudes of force associated with touch events applied to the cover 104. The touch and/or force sensors may detect various types of user inputs to control or modify the operation of the device, including taps, swipes, multiple finger inputs, single- or multiple-finger touch gestures, presses, and the like. Touch and/or force sensors usable with wearable electronic devices, such as the device 100, are described below.

The electronic device 100 may also include a crown 108 having a cap, protruding portion, or component(s) or feature(s) (collectively referred to herein as a "body") positioned along a side surface of the housing 103. At least a portion of the crown 108 (such as the body) may protrude from, or otherwise be located outside, the housing 103, and may define a generally circular shape or circular exterior surface. The exterior surface of the body of the crown 108 may be textured, knurled, grooved, or otherwise have features that may improve the tactile feel of the crown 108 and/or facilitate rotation sensing.

The crown 108 may facilitate a variety of potential interactions. For example, the crown 108 may be rotated by a user (e.g., the crown may receive rotational inputs). Rotational inputs of the crown 108 may zoom, scroll, rotate, or otherwise manipulate a user interface or other object displayed on the display 106 (among other possible functions). The crown 108 may also be translated or pressed (e.g., axially) by the user. Translational or axial inputs may select highlighted objects or icons, cause a user interface to return to a previous menu or display, or activate or deactivate functions (among other possible functions). In some cases, the device 100 may sense touch inputs or gestures applied to the crown 108, such as a finger sliding along the body of the crown 108 (which may occur when the crown 108 is configured to not rotate) or a finger touching the body of the crown 108. In such cases, sliding gestures may cause operations similar to the rotational inputs, and touches on an end face may cause operations similar to the translational inputs. As used herein, rotational inputs include both rotational movements of the crown (e.g., where the crown is free to rotate), as well as sliding inputs that are produced when a user slides a finger or object along the surface of a crown in a manner that resembles a rotation (e.g., where the crown is fixed and/or does not freely rotate). In some embodiments, rotating, translating, or otherwise moving the crown 108 initiates a pressure measurement by a pressure-sensing system (such as an external and/or internal pressure-sensing device) located on or within the electronic device 100. In some cases, selecting an activity, requesting a location, specific movements of the user, and so on may also initiate pressure measurements by the pressures-sensing system.

The electronic device 100 may also include other inputs, switches, buttons, or the like. For example, the electronic device 100 includes a button 110. The button 110 may be a movable button (as depicted) or a touch-sensitive region of the housing 103. The button 110 may control various aspects of the electronic device 100. For example, the button 110 may be used to select icons, items, or other objects displayed on the display 106, to activate or deactivate functions (e.g., to silence an alarm or alert), or the like.

The electronic device 100 may include a band 112 coupled to the housing 103. The band may be configured to couple the electronic device 100 to a user, such as to the user's arm or wrist. A portion of the band 112 may be received in a channel that extends along an internal side of the housing 103, as described herein. The band 112 may be secure to the housing within the channel to maintain the band 112 to the housing 103.

Figure 2A:
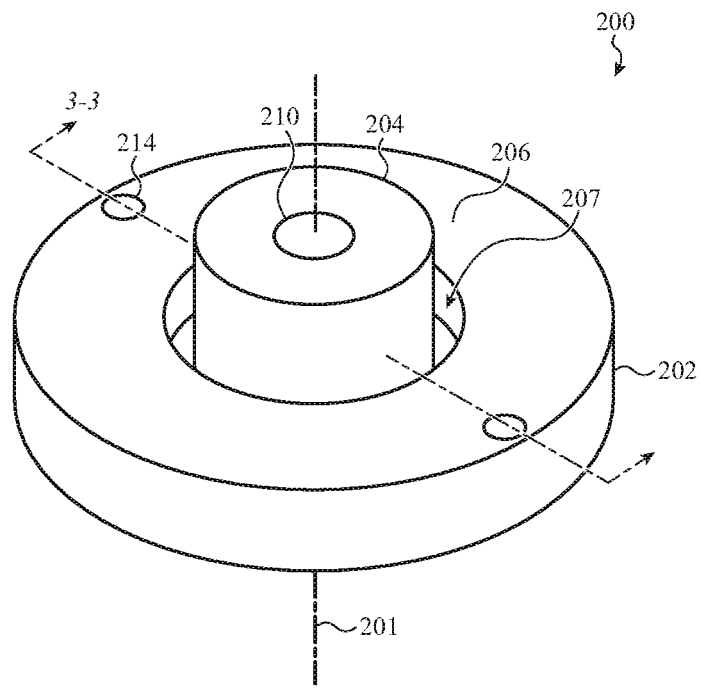
FIGS. 2A and 2B illustrate an example temperature sensing device that can be included in an electronic device.
Figure 2B:
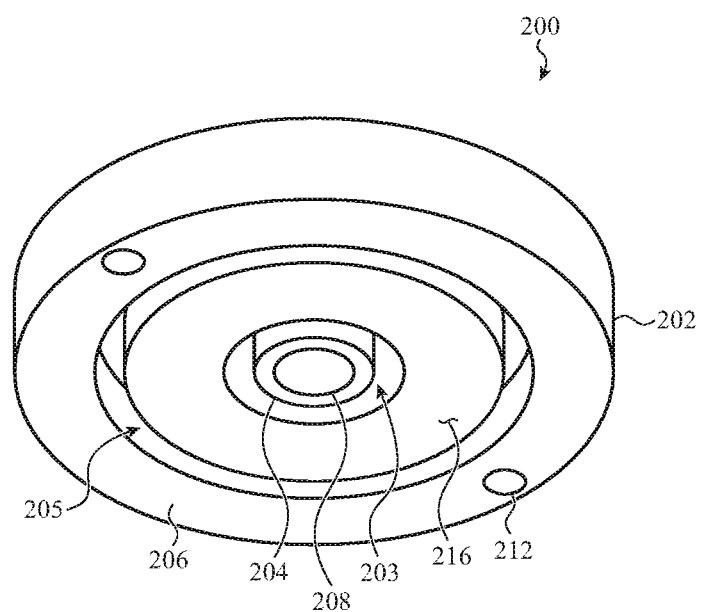

FIGS. 2A and 2B illustrate top and bottom perspective views, respectively, of a temperature sensing device 200 that can be included in an electronic device. The temperature sensing device 200 can be an example of the miniature dual heat flux temperature sensing devices described herein such as dual heat flux temperature sensing device 102. The temperature sensing device 200 can include a sensor body 202 that has a first section 204 having a first thickness (here, its height) and a second section 206 that has a second thickness (again, in this example its height) that is less than the first section 204. The temperature sensing device 200 can also include a first set of temperature sensors 208 and 210 that are configured to measure a temperature difference across the first thickness of the first section 204, and a second set of temperature sensors 212 and 214 that are configured to measure a temperature difference across the second thickness of the second section 206.

In some embodiments, the first section 204 is a cylindrical body forming an inner portion of the sensor body 202 and the second section 206 is also a cylindrical body (or more specifically, a toroidal body) forming an outer portion of the sensor body 202. The second section 206 can extend around the outside cylindrical surface of the first section 204. In some cases, the first section 204 and the second sections 206 can be formed from a single homogenous material to form a continuous sensor body 202. In other cases, the first section 204 and the second section 206 may be formed as separate bodies and joined together to form a single sensor body 202. The sensor body 202 can also include one or more channels such as channels 203, 205 and 207, which are located between the first section 204 and the second section 206. The channels may be formed in the sensor body 202 such that a depth of the channel extends partially through a thickness of the sensor body 202. Accordingly, the sensor body 202 can be a continuous and/or single structure that defines the first section 204, the second section 206 and one or more channels positioned between the first and second sections 204, 206.

The channels 203, 205 and 207 may be configured to reduce the heat transfer between the first section 204 and the second section 206. The channels can contain air (or other gas) that has a higher resistance to heat flow (lower heat transfer rate) than the sensor body. In this regard, the first channel 203 can separate the first lower surface of the first section 204 from the second lower surface of the second section 206 to reduce heat between these portions of the sensor body 202. In some cases, the sensor body 202 defines a single channel (e.g., first channel 203) positioned along a lower surface between the first section 204 and the second section 206. In some embodiments, the sensors body can define additional channels between the first section 204 and the second section 206. For example, the sensor body 202 can be formed to define a second channel 205 between the first and second sections 204 and 206. In this regard, the sensor body 202 can have a third lower surface 216 that is positioned between the first lower surfaces of the first section 204 and second lower surface of the second section 206. Additionally or alternatively, the sensor body 202 can be formed to define a third channel 207 that is positioned between the first upper surface of the first section 204, and the second upper surface of the second section 206.

As illustrated in FIGS. 2A and 2B, the sensor body 202 can be radially symmetric about an axis 201 and the channels 203, 205 and/or 207 can extend in a circular configuration around the axis 201 (e.g., they may be ring-shaped). In other embodiments, the sensor body 202 can be formed in other configurations such as a square, or other polygon configurations.

As illustrated in FIG. 2B, a first temperature sensor 208 can be located on a first lower surface of the sensor body 202 corresponding to the first section 204. As illustrated in FIG. 2A, a second temperature sensor 210 can be located on a first upper surface of the sensor body 202 also corresponding to the first section 204. The first and second temperature sensors 208, 210 can form a first set of temperature sensors and be configured to measure temperatures of the sensor body 202 at the corresponding first lower surface and first upper surface. Also, as illustrated in FIGS. 2A and 2B, a third temperature sensor 212 can be located on a second lower surface of the sensor body 202 corresponding to the second section 206, and a fourth temperature sensor 214 can be located on a second upper surface also corresponding to the second section 206. The third and fourth temperature sensors 212, 214 can form a second set of temperature sensors and be configured to measure temperatures of the sensor body 202 at the corresponding second lower surface and second upper surface. In some cases, additional temperature sensors can be positioned at various points on the sensor body 202. For example, multiple sets of temperature sensors (not shown) can be positioned around the second section 206, and may be used in coordination with the second set of temperature sensors 212, 214 to increase accuracy of temperature measurements at a periphery of the sensor body 202.

In some embodiments, the temperature sensors 208 and 212 are positioned on the sensor body 202 such that they are flush with the surface of the sensor body 202. Such a configuration may result in even heat transfer from the body to both of the temperature sensors 212, 214 and the sensor body 202. In other embodiments, the temperature sensors 208 and 212 protrude from the sensor body 202 or are positioned on the sensor body 202 such that they are raised from the surface of the sensor body 202. Such a configuration can help the temperature sensors 208 and 212 contact a skin of the user to obtain good heat transfer between the skin and the temperature sensors 208 and 212.

Figure 3:
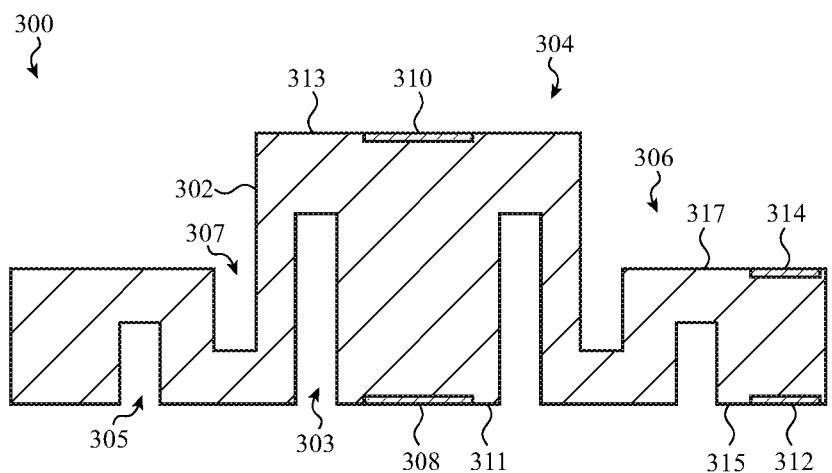
FIG. 3 is a cross-sectional view of an example temperature sensing device.

FIG. 3 illustrates a cross-sectional view taken along section A-A of FIG. 2A of a temperature sensing device 300. The temperature sensing device 300 can include a sensor body 302, which may be an example of the sensor bodies described herein (e.g., sensor body 202). The sensor body 302 can define a first section 304, a second section 306, and one or more channels 303, 305, 307. The temperature sensing device 300 can also include a first temperature sensor 308, a second temperature sensor 310, a third temperature sensor 312, and a fourth temperature sensor 314, which may be examples of the temperature sensors described herein.

The sensor body 302 can be formed, machined, or otherwise shaped to define the first, second, and/or third channels 303, 305 and 307. In some cases, a depth of the first channel 303 can extend from the first lower surface 311 of the first section 304 and toward to the first upper surface 313 of the first section 304. The first channel 303 can contain air (or other gas), or other insulating material between the first section 304 and the second section 306, that results in a thermal break that decreases the heat transfer rate (increases the thermal resistance) between the first section 304 and the second section 306. In this regard, when the first lower surface 311 is placed on a skin of a user, heat transferred to the first section 304 from the user is at least partially isolated from the second section 306. Accordingly, the first channel 303 at least partially thermally isolates the first section 304 from the second section 306 of the sensor body 302 such that the effect of heat flow occurring at the first section (from the first lower surface 311 to the first upper surface 313) on the second section 306 is reduced as compared to devices without a channel separating the lower surfaces. Similarly, the effect of heat flow occurring at the second section (from the second lower surface 315 to the second upper surface 317) on the first section 304 is reduce by the first channel 303.

In some embodiments, a depth of the second channel 305 can extend from the second lower surface 315 and toward the second upper surface 317. Similar to the first channel 303, the second channel 305 can thermally isolate the first section 304 from the second section 306. In some embodiments, the sensor body can include a single channel (e.g., first channel 303 or second channel 305). In other embodiments, the sensor body 302 can include multiple channels such as both the first channel 303 and the second channel 305, which may result in greater thermal isolation between the first section 304 and the second section 306. Additionally or alternatively, the sensor body 302 can include the third channel 307, which can extend from the second upper surface 317 and toward the second lower surface 315.

Figure 4:
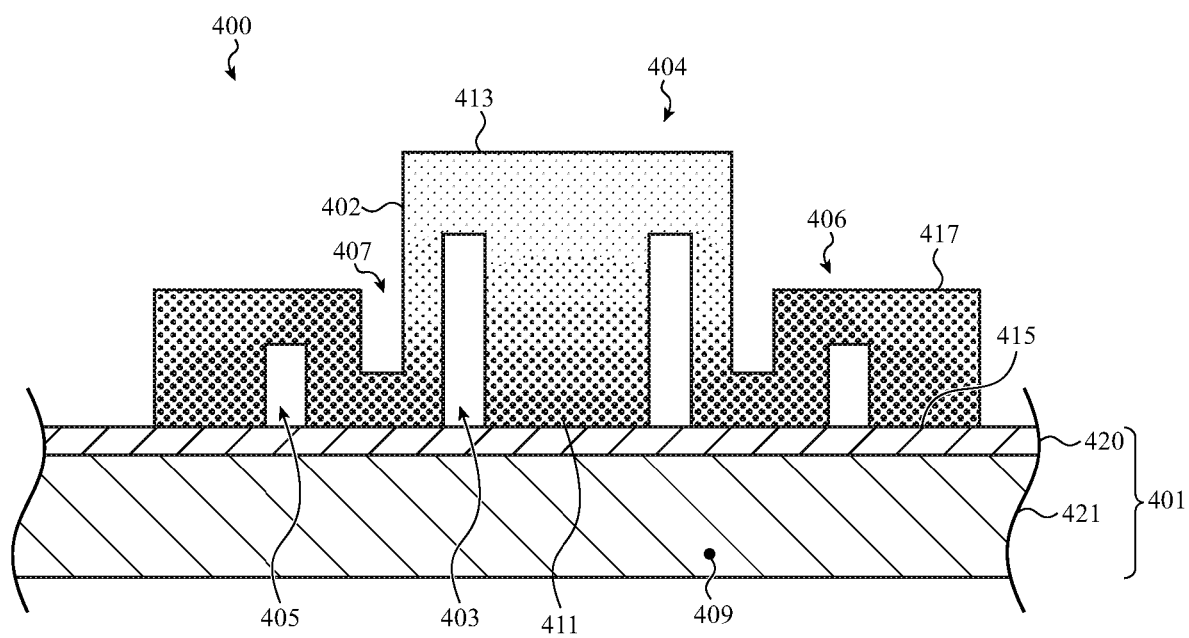
FIG. 4 is a cross-sectional view showing a temperature distribution of an example temperature sensing device.

FIG. 4 illustrates a cross-sectional view taken along section A-A of FIG. 2A showing an example temperature gradient across a temperature sensing device 400. The temperature sensing device 400 can be an example of the temperatures sensing devices described herein (e.g., temperature sensing devices 102, 200, and 300). The temperature sensing device 400 can include a sensor body 402 including a first section 404, a second section 406, and defining a first channel 403, a second channel 405 and a third channel 407. FIG. 4 illustrates the temperature sensing device 400 placed on the skin 420 of a user 401 and being used to estimate a subsurface temperature 409 associated with deep tissue 421 of a user 401. FIG. 4 also illustrates an example heat gradient across the sensor body 402, with larger circles representing higher temperatures. As shown in FIG. 4, the channels 403, 405 and 407 thermally isolate the first section 404 from the second section 406. For example, the channels 403, 405 and 407 create a longer, serpentine path that heat has to travel to be transferred between the first section 404 and the second section 406.

In some cases, the skin 420 of the user 401 is at a lower temperature than tissue 421 below the skin 420. As used herein, the term "subsurface temperature" 409 refers to the temperature of tissue that is located below the skin surface 420, for example tissue located below an epidermis layer of the skin. In some embodiments, the temperature sensing device 400 can measure a temperature at the skin 420 and use these measurements to estimate the subsurface temperature 409 of the user.

For example, the temperature sensing device 400 can measure a temperature across the thickness of the first section 404, for example, by determining a first temperature difference between the first lower surface 411 and the first upper surface 413. The temperature sensing device 400 can also measure a temperature across the thickness of the second section 406, for example, by determining a second temperature difference between the second lower surface 415 and the second upper surface 417. A different temperature between the first section 404 and the second section 406 can be used to estimate the subsurface temperature 409.

By way of example, $T_1$ can be a first temperature measured at the first lower surface 411, $T_2$ can be a second temperature measured at the second lower surface 415, $T_3$ can be a third temperature measured at the first upper surface 413 and $T_4$ can be a fourth temperature measured at the second upper surface 417. The following equation can be used to estimate the subsurface temperature 409 ($T_{subsurface}$):

$$T_{Subsurface} = T_1 + \frac{(T_1 - T_2)(T_1 - T_3)}{K(T_2 - T_4) - (T_1 - T_3)}$$

Where K represent the ratio of the thermal conductivity between the thermal conductivity ($K_1$) of the first section 404 and the thermal conductivity ($K_2$) of the second section 406, and can be determined using the following equation:

$$K = \frac{K_1}{K_2}$$

As illustrated in FIG. 4, the temperature sensing device 400 is operative to increase the unidirectional heat flow from the bottom surfaces 411 and 415 to the top surfaces 413 and 417 (e.g., heat flow perpendicular to the skin surface), and decrease heat flow between the first section 404 and the second section 406. For example, thermally isolating the first section 404 from the second section 406, as described herein, can result in a higher thermal gradient between these sections, which can increase the accuracy of the subsurface temperature measurement.

Figure 5:
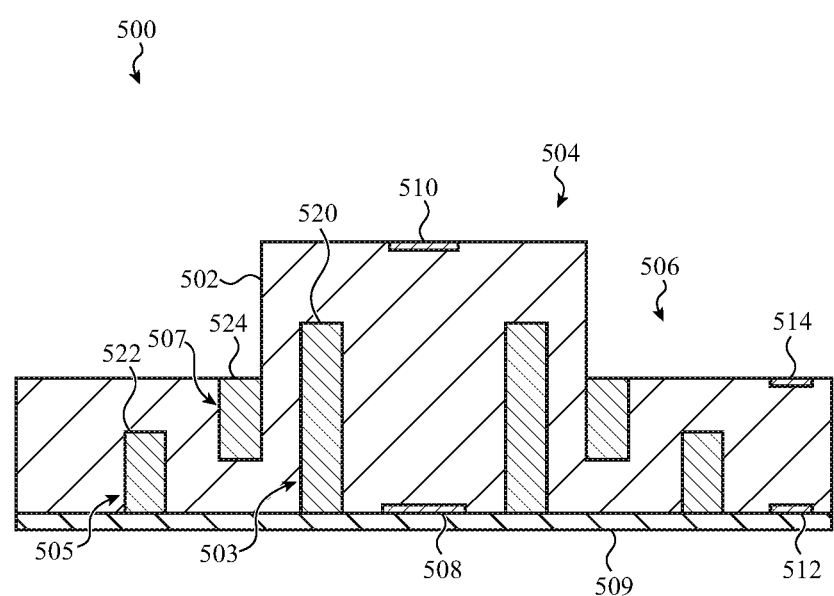
FIG. 5 is a cross-sectional view of an example temperature sensing device.

FIG. 5 illustrates a cross-sectional view taken along section A-A of FIG. 2A of a temperature sensing device 500. The temperature sensing device 500 can be an example of the temperature sensing device described herein (e.g., temperature sensing devices 102, 200, 300, and 400), and include a sensor body 502 comprising a first section 504 and a second section 506, as described herein. The sensor body 502 can define a first channel 503, a second channel 505 and a third channel 507, which can be examples of the channels described herein. The temperature sensing device 500 can also include a first temperature sensor 508, a second temperature sensor 510, a third temperature sensor 512 and a fourth temperature sensor 514.

In some embodiments, the temperature sensing device 500 can be positioned on and/or coupled to a substrate 509, and the substrate 509 may be positioned against a skin of a user. In some cases, the substrate 509 can be a portion of an electronic device, for example a housing element, such as a wall, cover or peripheral structure of the device that positions the temperature sensing device 500 in proximity to a skin surface of a user. In some examples, the substrate can be a conductive material such as metal, plastic, composite material or any other suitable material.

In some embodiments, the temperature sensors 508, 510, 512, and 514 can include thin film temperature sensors such as a thin film resistance temperature detector (RTD), negative thermal coefficient (NTC) temperature sensors, thermocouples, thermopiles, or other suitable temperature sensing devices. In some cases, the temperature sensing device can include additional temperature sensors. For example, additional temperature sensors could be positioned around the upper and lower surfaces of the second section 506. In some cases, temperature measurements from various sensors can be combined, averaged, compared, or otherwise modified, and used to perform the subsurface temperature estimation techniques described herein.

In some embodiments, one or more of the channels 503, 505, and 507 can contain an insulating material. As used herein, "an insulating material" refers to materials that have a lower thermal conductivity (higher resistance to heat flow) than the material of the sensor body 502. For example, the first channel 503 can contain a first insulating material 520, the second channel 505 can contain a second insulting material 522, and the third channel 507 can contain a third insulating material 524. The first, second and third insulating materials 520, 522, and 524 can be the same or different. Examples of insulating materials can include air (as described herein); other gases; a vacuum where air is removed from the channels 503, 505 and/or 507; materials such as fiber glass, mineral wool, cellulose, and so on.

FIGS. 6A-6D show cross-sectional views taken along line A-A of FIG. 2A of example temperature sensing devices 600. The temperature sensing devices 600 can be examples of the temperature sensing device described herein (e.g., temperature sensing devices 102, 200, 300, 400, and 500), and include a sensor body 602 comprising a first section 504 and a second section 506. The sensor body 602 can define a first channel 603, a second channel 605 and a third channel 607, which can be examples of the channels described herein. The temperature sensing device 600 can also include temperature sensors as described herein.

Figure 6A:
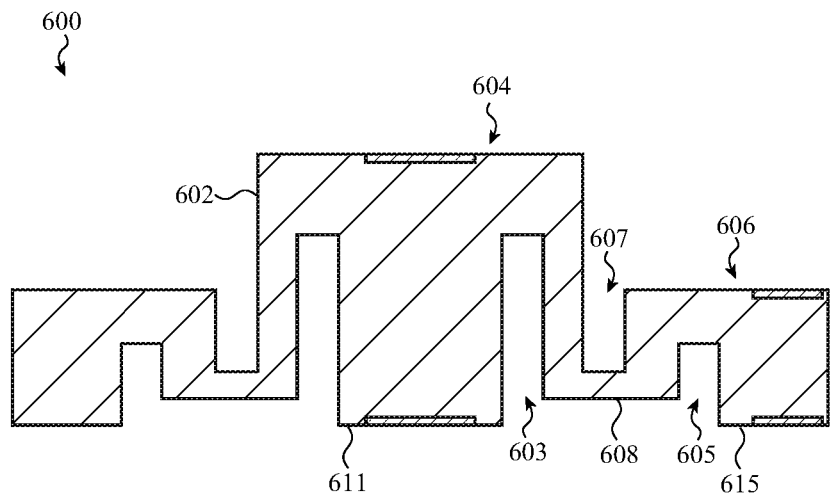
FIGS. 6A-6D show cross-sectional views of example temperature sensing devices.

In the example shown in FIG. 6A, the sensor body 602 can define a third section 608 that connects the first section 604 to the second section 606. The third section 608 can be offset from the lower surfaces 611 and 615 such that when the temperature sensing device 600 is placed against a user, the first and second surfaces 611 and 615 contact the user or a substrate (e.g., substrate 509), while the third section 608 does not contact the user or the substrate. This configuration may reduce heat transfer from the user to the third section 608, which can reduce heat flow that occurs between the first section 604 and the second section 606.

Figure 6B:
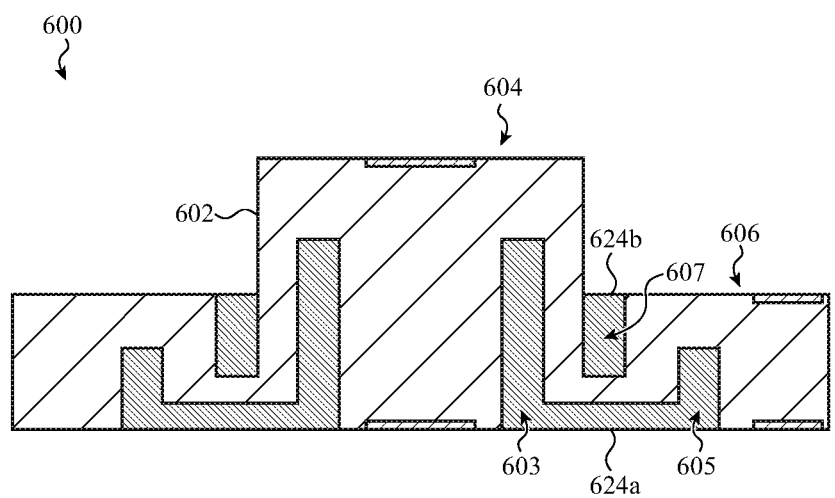

In the example shown in FIG. 6B, the temperature sensing device 600 can include an insulating material 624 within one or more of the channels 603, 605 and 607. For example, The sensor body 602 can define a raised third section 608 that connects the first and second sections 604 and 606 as described in reference to FIG. 6A. In some cases, a first insulating material 624a can be positioned within the first channel 603, the second channel 605 and space created by the raised third section 608. In some cases, the third channel 607 can also contain a second insulating material 624b, which can be the same or different as the first insulating material 624a. The insulating materials 624 can have lower heat transfer rate than the sensor body 602. In some cases, the insulating materials 624 can include air, a vacuum, foams or other lower resistance materials such glass, plastics, ceramics, and so on.

Figure 6C:
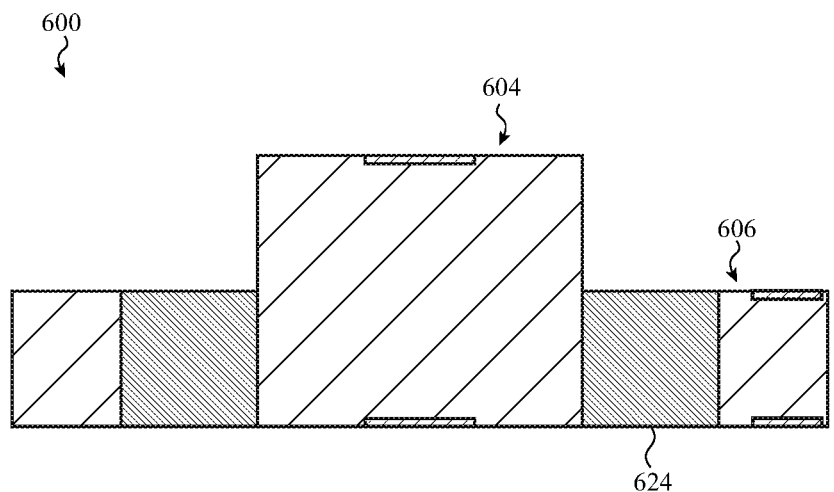

In the example shown in FIG. 6C, the temperature sensing device 600 can include an insulating material 624 that is positioned between the first and second sections 604 and 606, and separates the first section 604 from the second section 606. In some embodiments, the insulating material 624 can couple the first section 604 to the second section 606. In the example shown in FIG. 6C, the insulating material 624 can extend to the height of the second section 606. The insulating material 624 can include insulating materials as described herein, such as foams, ceramics, glasses, plastics, composite materials, and so on that have a lower heat transfer rate than the material forming the first and second sections 604 and 606.

Figure 6D:
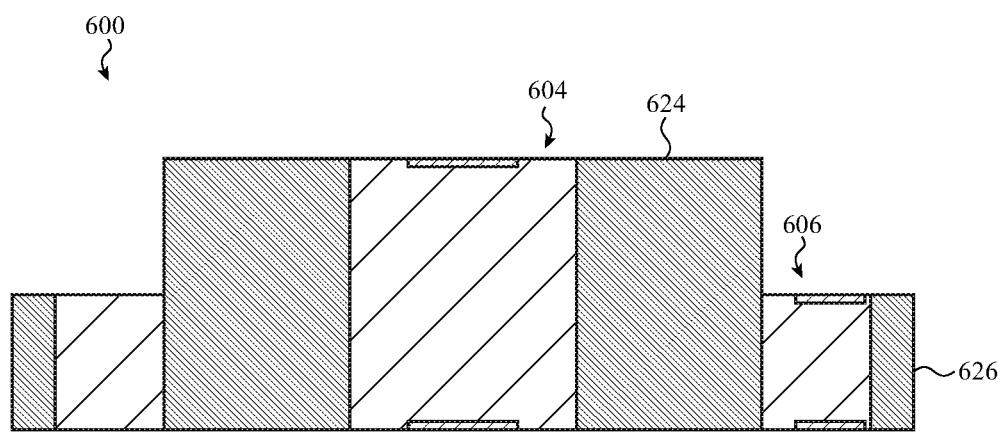

In the example shown in FIG. 6D, the temperature sensing device 600 can include an insulating material 624 that is positioned between the first and second sections 604 and 606, and separates the first section 604 from the second section 606. The insulating material 624 can extend to the height of the first section 604, which may increase unidirectional heat flux by insulating the first section 604 from the surrounding environment. In other cases, the temperature sensing device 600 can include a second insulating material 626 that surrounds the second section 606. Additionally or alternatively, the insulating materials can fully or partially encapsulate the temperature sensing device 600, or selectively cover different portions of the temperature sensing device, which may be configured to increase the unidirectional heat flux across the first section 604 and the second section 606 and decrease heat transfer between the first and second sections 604 and 606.

Figure 7:
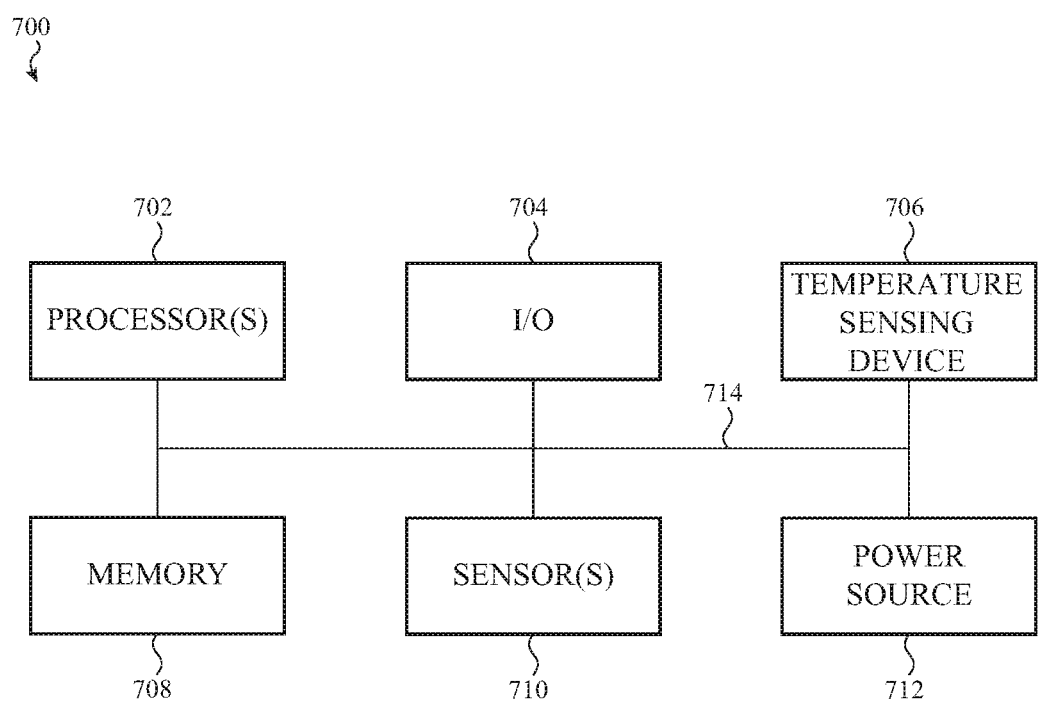
FIG. 7 is a block diagram illustrating an example electronic device, which can incorporate a temperature sensing device.

FIG. 7 is a block diagram illustrating an example electronic device 700, which can take the form of any of the electronic devices incorporating a dual heat flux temperature sensing device as described with reference to FIGS. 1-5. The optical device can include a processor 702, an input/output (I/O) mechanism 704 (e.g., an input/output device, such as a touch screen, crown or button, input/output port, or haptic interface), one or more temperature sensors 706, memory 708, other sensors 710 (e.g., an optical sensing system, barometric pressure sensors, etc.), and a power source 712 (e.g., a rechargeable battery). The processor 702 can control some or all of the operations of the electronic device 700. The processor 702 can communicate, either directly or indirectly, with some or all of the components of the electronic device 700. For example, a system bus or other communication mechanism 714 can provide communication between the processor 702, the I/O mechanism 704, the dual heat flux temperature sensing device 706, the memory 708, the sensors 710, and the power source 712.

The processor 702 can be implemented as any electronic device capable of processing, receiving, or transmitting data or instructions. For example, the processor 702 can be a microprocessor, a central processing unit (CPU), an application-specific integrated circuit (ASIC), a digital signal processor (DSP), or combinations of such devices. As described herein, the term "processor" is meant to encompass a single processor or processing unit, multiple processors, multiple processing units, or other suitable computing element or elements.

It should be noted that the components of the electronic device 700 can be controlled by multiple processors. For example, select components of the electronic device 700 (e.g., a sensor 710) may be controlled by a first processor and other components of the electronic device 700 (e.g., the temperature sensing device 706) may be controlled by a second processor, where the first and second processors may or may not be in communication with each other.

The I/O mechanism 704 can transmit and/or receive data from a user or another electronic device. An I/O device can include a display, a touch-sensing input surface, one or more buttons (e.g., a graphical user interface "home" button), one or more cameras, one or more microphones or speakers, one or more ports, such as a microphone port, and/or a keyboard. Additionally or alternatively, an I/O device or port can transmit electronic signals via a communications network, such as a wireless and/or wired network connection. Examples of wireless and wired network connections include, but are not limited to, cellular, Wi-Fi, Bluetooth, IR, and Ethernet connections.

The temperature sensing device 706 can be any of, or include a combination of features of the dual heat flux temperature sensing devices described herein, such as temperature sensing devices 100, 200, 300, 400, 500 or 600. In some cases, the electronic device 700 can include multiple temperature sensing devices 706 that are positioned at various locations of the electronic device 700. For example, one or more temperature sensing devices 706 can be configured to estimate a subsurface temperature of an external subject such as a deep tissue temperature of a user. Additionally or alternatively, one or more temperature sensing devices 706 can be operative to measure a subsurface temperature of one or more internal components, such as a processor (e.g., processor 702), memory (e.g., memory 708), and so on.

The memory 708 can store electronic data that can be used by the electronic device 700. For example, the memory 708 can store electrical data or content such as, for example, audio and video files, documents and applications, device settings and user preferences, timing signals, control signals, and data structures or databases. The memory 708 can be configured as any type of memory. By way of example only, the memory 708 can be implemented as random access memory, read-only memory, Flash memory, removable memory, other types of storage elements, or combinations of such devices.

The electronic device 700 may also include one or more sensors 710 positioned almost anywhere on the electronic device 700. The sensor(s) 710 can be configured to sense one or more type of parameters, such as but not limited to, pressure, light, touch, heat, movement, relative motion, biometric data (e.g., biological parameters), and so on. For example, the sensor(s) 710 may include a heat sensor, a position sensor, a light or optical sensor, an accelerometer, a pressure transducer, a gyroscope, a magnetometer, a health monitoring sensor, and so on. Additionally, the one or more sensors 710 can utilize any suitable sensing technology, including, but not limited to, capacitive, ultrasonic, resistive, optical, ultrasound, piezoelectric, and thermal sensing technology.

The power source 712 can be implemented with any device capable of providing energy to the electronic device 700. For example, the power source 712 may be one or more batteries or rechargeable batteries. Additionally or alternatively, the power source 712 can be a power connector or power cord that connects the electronic device 700 to another power source, such as a wall outlet.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not targeted to be exhaustive or to limit the embodiments to the precise forms disclosed. It will be apparent to one of ordinary skill in the art that many modifications and variations are possible in view of the above teachings.

What is claimed is:

1. A temperature measurement device, comprising:
    a sensor body configured to be placed on a skin of a user, the sensor body comprising:
        a first section defining a first upper surface and a first lower surface and having a first thickness;
        a second section defining a second upper surface and a second lower surface and having a second thickness;
        a first channel separating between the first lower surface from and the second lower surface; and
        a second channel between the first upper surface and the second upper surface:
    a first set of temperature sensors positioned across the first thickness;
    a second set of temperature sensors positioned across the second thickness; and
    a processor configured to estimate a tissue temperature of the user based on comparing temperature signals from the first set of temperature sensors with temperature signals from the second set of temperature sensors.

2. The temperature measurement device of claim 1, wherein:
    the sensor body further defines:
        a third lower surface positioned between the first and second lower surfaces; and
        a second channel;
    the first channel is between the first lower surface and the third lower surface; and
    the second channel is between the second lower surface and the third lower surface.

3. The temperature measurement device of claim 2, wherein:
    the first set of temperature sensors has a first temperature sensor positioned on the first lower surface and a second temperature sensor positioned on a first upper surface of the first section; and
    the second set of temperature sensors has a third temperature sensor positioned on the second lower surface and a fourth temperature sensor positioned on a second upper surface of the second section.

4. The temperature measurement device of claim 1, wherein:
    the first section defines an upper surface opposite the first lower surface; and
    a depth of the channel extends towards the upper surface.

5. The temperature measurement device of claim 1, wherein:
the first section defines a first cylindrical body; and
the second section defines a second cylindrical body.

6. The temperature measurement device of claim 5, wherein the second section extends around the first section.

7. The temperature measurement device of claim 1, wherein:
the sensor body is symmetric about an axis; and
the channel extends in a circle around the axis.

8. The temperature measurement device of claim 1, wherein:
the sensor body comprises a conductive material; and
the channel contains an insulating material.

9. The temperature measurement device of claim 1, further comprising a substrate positioned on the first and second lower surfaces and configured to contact the skin of the user.

10. A temperature sensor, comprising:
a sensor body for measuring a temperature of a user, the sensor body comprising:
a first section defining a first lower surface that is offset from a first upper surface;
a second section defining a second lower surface that is offset from a second upper surface, wherein a first thickness between the first lower surface and the first upper surface is greater than a second thickness between the second lower surface and the second upper surface; and
a first channel between the first lower surface and the second lower surface;
a second channel between the first upper surface and the second upper surface:
a first set of temperature sensors positioned on the first section;
a second set of temperature sensors positioned on the second section; and
a processor configured to estimate a tissue temperature of the user based on comparing temperature signals from the first set of temperature sensors with temperature signals from the second set of temperature sensors.

11. The temperature sensor of claim 10, wherein:
the first set of temperature sensors includes a first sensor positioned on the first lower surface and a second sensor positioned on the first upper surface; and
the second set of temperature sensors includes a third sensor positioned on the second lower surface and a fourth sensor positioned on the second upper surface.

12. The temperature sensor of claim 10, wherein the first and second lower surfaces are configured to be placed against a skin of the user.

13. The temperature sensor of claim 10, wherein the sensor body further defines:

a third lower surface that is separated from the first lower surface by the first channel; and
a third channel that separates the third lower surface from the second lower surface.

14. The temperature sensor of claim 10, wherein the sensor body is a conductive material and the first channel comprises insulating material.

15. The temperature sensor of claim 10, wherein first section forms a central part of the sensor body and the second section forms an outer part of the sensor body.

16. A temperature sensor, comprising:
a sensor body for measuring a temperature of a user, the sensor body defining:
first and second lower surfaces that are configured to be placed against a skin of the user;
a first upper surface offset from and opposite the first lower surface;
a second upper surface offset from and opposite the second lower surface, wherein a first thickness between the first lower surface and the first upper surface is greater than a second thickness between the second lower surface and the second upper surface; and
a first channel positioned between the first and second lower surfaces;
a second channel positioned between the first and second upper surfaces:
a set of temperature sensors that are configured to measure temperatures at the first lower surface, the second lower surface, the first upper surface, and second upper surface; and
a processer configured to estimate a tissue temperature of the user based on the temperature measurements from the set of temperature sensors.

17. The temperature sensor of claim 16, wherein the sensor body further defines:
a third lower surface positioned between the first and second lower surfaces; and
a third channel positioned between the first and second lower surfaces.

18. The temperature sensor of claim 17, wherein the set of temperature sensors comprises:
a first temperature sensor positioned on the first lower surface;
a second temperature sensor positioned on the first upper surface;
a third temperature sensor positioned on the second lower surface; and
a fourth temperature sensor positioned on the second upper surface.

19. The temperature sensor of claim 16, wherein:
the sensor body comprises a conductive material; and
the channel comprises an insulating material.

* * * * *

UNITED STATES PATENT AND TRADEMARK OFFICE
CERTIFICATE OF CORRECTION

| | | |
|---|---|---|
| PATENT NO. | : 11,635,334 B2 | Page 1 of 1 |
| APPLICATION NO. | : 16/917704 | |
| DATED | : April 25, 2023 | |
| INVENTOR(S) | : Helia Rahmani et al. | |

It is certified that error appears in the above-identified patent and that said Letters Patent is hereby corrected as shown below:

In the Claims

Column 14; Line 30; Claim 1:
"a first channel separating between the first lower sur-"
Should read as:
--a first channel between the first lower sur- --

Column 14; Line 31; Claim 1:
"face from and the second lower surface; and"
Should read as:
--face and the second lower surface; and--

Signed and Sealed this
Sixth Day of June, 2023

Katherine Kelly Vidal
*Director of the United States Patent and Trademark Office*